United States Patent [19]

Hashiue et al.

[11] Patent Number: 4,640,759
[45] Date of Patent: Feb. 3, 1987

[54] SUPPORTED MEDIUM FOR ELECTROPHORESIS AND SUPPORTS THEREFOR

[75] Inventors: Masakazu Hashiue, Kaisei; Masashi Ogawa, Asaka, both of Japan

[73] Assignee: Fuji Photo Film Co., Ltd.

[21] Appl. No.: 710,130

[22] Filed: Mar. 11, 1985

[30] Foreign Application Priority Data

Mar. 12, 1984 [JP] Japan ................................. 59-47556
Apr. 20, 1984 [JP] Japan ................................. 59-79612

[51] Int. Cl.$^4$ ....................................... G01N 27/28
[52] U.S. Cl. .............................. 204/299 R; 204/182.8
[58] Field of Search ............. 204/299 R, 182.8, 180 G

[56] References Cited

U.S. PATENT DOCUMENTS 4,194,963  3/1980  Denckla .......................... 204/299 R
4,309,268  1/1982  Richman ........................... 204/301
4,415,418  11/1983 Turre et al. ................. 204/299 R X

OTHER PUBLICATIONS

"Introducing Repliplate", FMC Catalog, ©1984.

Primary Examiner—John F. Niebling
Assistant Examiner—B. J. Boggs, Jr.
Attorney, Agent, or Firm—Toren, McGeady & Goldberg

[57] ABSTRACT

A process for electrophoresis employing a medium wherein the potential gradient along the direction of electrophoresis is made larger at both side portions of the medium than at the center portion thereof. A medium for employable for said process in that the length of the both side portions along the direction of electrophoresis is made shorter than that of the center portion is disclosed. Also disclosed is a support for the medium.

8 Claims, 10 Drawing Figures

FIG. 5
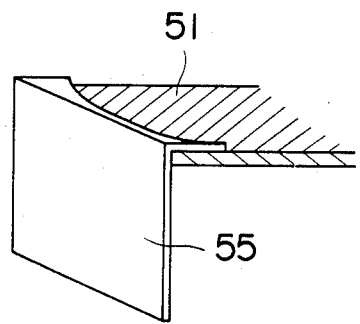
FIG. 6a    FIG. 6b    FIG. 6c
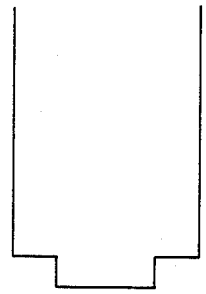  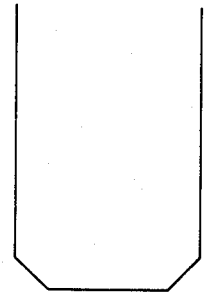  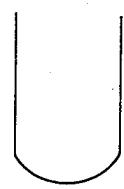

SUPPORTED MEDIUM FOR ELECTROPHORESIS AND SUPPORTS THEREFOR

BACKGROUND OF THE INVENTION

1. Field of the Invention

This invention relates to a process for electrophoresis, medium employable therefor and a support for preparing and/or supporting the medium.

2. Description of Prior Arts

There has been heretofore known electrophoresis for separating proteins, decomposition products of protein, nucleic acids, and decomposition products of nucleic acid by means of a sheet-type medium such as a gel membrane or filter paper impregnated with a buffer solution, which is based on phenomenon that the charged particles of said substances migrate under the influence of the electric field. Particularly, electrophoresis has been advantageously performed for the purposes of separation and identification of biopolymers as mentioned above.

In the genetic engineering field which has been paid more attention recently, the electrophoresis is regarded inevitable for determination of base sequence of nucleic acids such as DNA. Electrophoresis performed for the above purpose generally includes a process of causing a plurality of mixtures of radioactively labeled DNA or mixtures of base specifically cleaved products of DNA to migrate in parallel along the longitudinal direction of a medium for electrophoresis. The base sequence is determined by comparing a plurality of thus obtained electrophoretic patterns (an aggregate of zones (or bands) formed in a medium by electrophoresis.) This process is based on a principle that the base specifically cleaved products having the same molecular weight would migrate to the same positions as each other, as far as the starting positions for the electrophoresis procedure is the same as each other.

In the practical runs of electrophoresis, however, the substances having the same molecular weight are apt to migrate to the different positions. Therefore, the respective migration distances of the substances are not equal. In other words, the migration rate of charged substance is generally apt to be lower at the both side portions than at the central portion, and therefore, the pattern of electrophoresis after a lapse of certain time shows that the migration distance is shorter at both side portions than at the center portion as shown in FIG. 1. FIG. 1 is a schematic view of electrophoresis patterns of zones 13 and 13' obtained by electrophoresis starting from a starting point 12 on a medium 11. This phenomenon is called the "smiling effect". The smiling effect reduces the accuracy of the result obtained by the determination process of base sequence of DNA which involves a procedure of comparing a plurality of rows (i.e., lane) of electrophoresis.

The smiling effect is mainly caused by a difference in temperature between the center portion and side portion which is brought about by escape due to radiation of heat generated in the medium (Joule's heat) from the side edge portions. In more detail, while at the center portion of the medium the generated Joule's heat radiates from the upper and bottom surfaces, at the side edge portions Joule's heat radiates not only from the upper and bottom surfaces but also from the side edge portion. In order to compensate for the heat radiation, heat moves in the lateral (width) direction. The heat radiation can be easily compensated at the center portion of a medium because heat comes in from both sides. On the other hand, heat radiation cannot be fully compensated at the both sides because heat comes in from only one side. For these reasons, the temperature at the side portions is apt to be lower than at the center portion. In order to prevent generation of the smiling effect, a heat radiation plate is generally provided over the surface of an electrophoresis medium so as to reduce the difference of temperature. However, it is difficult to completely prevent the smiling effect by this method. Moreover, it is difficult to adapt the heat radiation plate to the electrophoresis medium.

SUMMARY OF THE INVENTION

An object of the present invention is to provide a process for electrophoresis capable of preventing or reducing the smiling effect which is apt to be generated in the procedure of electrophoresis wherein a plurality of electrophoresis rows are to be formed on one medium, and to provide a medium advantageously employable in the above process for electrophoresis.

In one aspect, the present invention resides in a process for electrophoresis wherein the potential gradient in the migration direction of a medium is made larger at both side portions of a medium than at the center portion thereof.

In another aspect, the invention resides in a medium suitable for performing the above process for electrophoresis characterized in that both side portions thereof in the migration direction are shorter than the center portion.

In still another aspect, the invention resides in a support suitable for preparing and/or supporting the above electrophoresis medium characterized in that the both side portions of the support along the migration direction are shorter than the center portion thereof.

In the specification, the term "both side portions of the medium" means both side portions outside of the effective area of the medium, that is, side portions outside of the the entire area where a plurality of electrophoresis rows are formed. Accordingly, said term does not always mean both side edge portions of the medium.

BRIEF DESCRIPTION OF THE DRAWINGS

FIG. 5 is a partial perspective view showing an example of a combination of a medium for electrophoresis suitable for the process of electrophoresis of the invention and a buffer connecting member.

FIGS. 6a, 6b and 6c are schematic views showing other examples of the shape of the medium for electrophoresis of the invention.

DETAILED DESCRIPTION OF THE INVENTION

The present invention will be described in detail with reference to the attached drawings.

As mentioned above, the process for electrophoresis according to the invention is characterized in that the potential gradient at the both side portions of a medium along the direction of electrophoresis is made larger than that at the center portion. In order to perform the above process for electrophoresis, a medium which is so made as to be longer at both side portions along the direction of electrophoresis than at the center portion can be employed.

Figure 1:
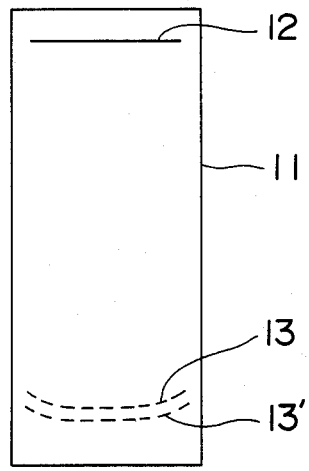
FIG. 1 is a schematic view showing a smiling effect appearing on a conventional medium for electrophoresis.
Figure 2:
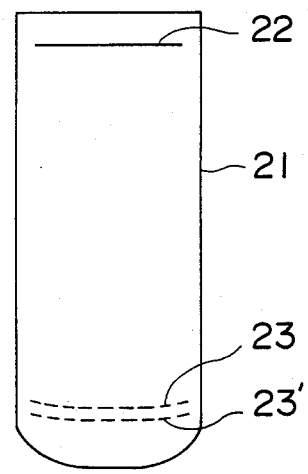
FIG. 2 is a schematic view of a pattern of electrophoresis appearing on a medium for electrophoresis according to the present invention.
Figure 3:
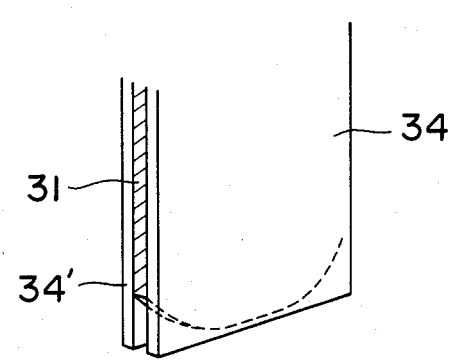
FIG. 3 is a partial perspective view showing an example of combination of a medium for electrophoresis and a support for supporting the medium advantageously employable for the process of electrophoresis according to the invention.

A medium shaped as shown in FIG. 2 in which both surfaces of a medium 31 are water-tightly sandwiched by supports 34 and 34' such as a glass plate and plastic film as shown in FIG. 3 can be employed. The lower end portion of the medium 31 is immersed in a buffer solution in contact with an electrode in accordance with a known method, and the upper end portion thereof is brought into contact with a buffer solution in contact with an electrode in accordance with a known method, whereby the distance between the electrodes at the both side portions of the medium (effective interelectrode distance, that is, the distance between surfaces of the two buffer solutions in contact with the medium) is made smaller than the effective interelectrode distance at the center portion in the case that the potential difference between the two electrodes is kept constant. Accordingly, the potential gradient at the both side portions of the medium (potential gradient in the direction of electrophoresis of the medium) can be made larger than the potential gradient at the center portion. Since migration rate of a charged substance is in direct proportion to the potential gradient of the electric field where the charged substance is located, the migration rate of a charged substance in the vicinity of either side portion becomes higher than the migration rate of a charged substance observed in the use of a conventional medium of the same size as shown in FIG. 1. Therefore, the difference between the migration rate of charged substances in the vicinity of the both side portions and the migration rate of a charged substance of the same nature at the center portion becomes zero or becomes reduced. Thus, the generation of smiling effect is prevented or the smiling effect is reduced.

The lower end portions of the supports 34 and 34' for tightly supporting the both surfaces of the medium 31 are not required to be straight-lined as shown in FIG. 3, and may take an arc-shape same as the lower end portion of the medium 31.

Figure 4:
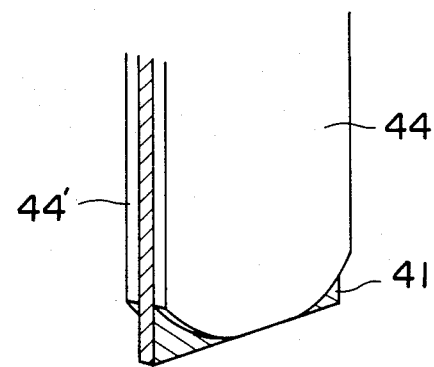
FIG. 4 is a partial perspective view showing another example of a combination of a medium for electrophoresis and a support for supporting the medium advantageously employable for the process of electrophoresis according to the invention.

As shown in FIG. 4, the combination of a medium 41 having a shape similar to the conventional one (see FIG. 1) and supports 44 and 44' for water-tightly sandwiching the both surfaces of the medium 41, each lower end portion of which takes an arc shape having a straight-lined portion in the area corresponding to the center portion of the medium can provide the desired difference of the potential gradient between at the side portions and center portion of the support.

Further, in the case that electrophoresis is performed using a horizontally placed medium, as shown in FIG. 5, a filter paper 55 (the lower end portion of which is connected to a buffer solution through a buffer connecting member) having a concave portion (e.g. a shape similar to that of the lower end portion of the medium as shown in FIG. 2) at the center portion of the upper end is placed in one end portion of a medium 51 which is shaped similar to the conventional one, so as to provide the desired difference between the potential gradient at the side portion and at center portion of the support.

The lower end portion of the medium for electrophoresis characterized in that the both side portions along the direction of electrophoresis are shorter than the center portion is not limited to a shape of an arc with its straight-lined portion at the center portion as shown in FIG. 2. For example, the lower end portion of the medium may take a simple form having its straight-lined protrusion at the center so as to make the both side portions shorter than the center portion as shown in FIGS. 6a and 6b. In the case that the medium is of a narrow shape, the lower end portion thereof may have a shape in a simple arc form as shown in FIG. 6c. Thus, the length of the medium may change in the width direction either continuously or intermittently.

There is no limitation on the nature of the medium for electrophoresis employable in the invention, and any of known media such as a filter paper, cellulose acetate membrane, starch gel membrane and polyacrylamide gel membrane can be employed. The polyacrylamide gel membrane is particularly preferred.

The medium for electrophoresis wherein the length of the both side portions along the direction of electrophoresis is made shorter than that at the center portion can be prepared simply by cutting a conventional medium. Further, a gel membrane such as a polyacrylamide gel membrane can be prepared by introducing a gel forming solution into a mold formed by placing a suitably shaped frame on a surface of a support such as a glass plate and plastic film or other plates and then hardening the solution.

In preparing a medium for electrophoresis in the invention, the desired difference between the length of the both side portions and that of the center portion can be experimentally determined.

Initially, a plurality of conventional rectangular mediums of the same size are independently formed on sheet-type supports made of plastic material or glass. Subsequently, the process of electrophoresis is performed under the predetermined conditions by employing one of the above mediums. Then, the degree of the smiling effect, that is, the difference of the migration distance between at both side portions and at center portion is measured on the obtained electrophoresis patterns. The exact difference or a value near the difference (a value little larger than the difference) is regarded as the desired difference between the length of the both side portions and that of the center portion. One end portion of each of other media can be so cut as to coincide with the difference. The support attached to the medium can be cut simultaneously with the medium or left uncut.

In another method, a suitable sheet-type support (e.g., mold) in which the length at the both side portions is made shorter than at the center portion (for instance, having the shape illustrated in FIG. 2) is prepared based on the correlation among the gel compositions, size of a medium, and conditions for electrophoresis obtained by repeating the above experiment. Then, on this support a gel membrane is formed to have the same shape as the shape of the employed support. For instance, gel membranes as shown in FIGS. 2, 6a, 6b and 6c can be formed using supports having the corresponding shapes.

Figure 7A:
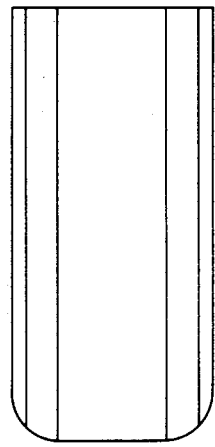
FIGS. 7a and 7b are schematic views showing examples of the shape of the support for the medium of electrophoresis of the invention.
Figure 7B:
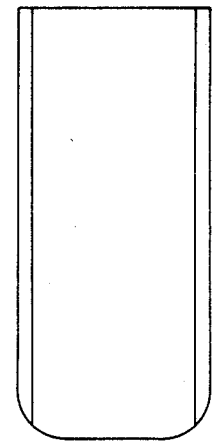
Figure 7B:
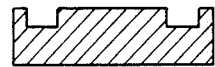
Figure 7B:
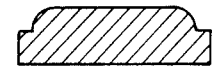

The support (i.e., mold) can be shaped as shown in FIGS. 7a and 7b, in which the support possessing shorter side portions have thicker central portion, that is, the thickness in the vicinity of the center thereof is larger than in both sides thereof. A medium prepared using this mold not only has shorter side portions but also has thicker side portions. The thicker side portions are effective to produce more Joule's heat therein under operational conditions of electrophoresis. Accordingly, a medium for electrophoresis prepared on a support (i.e., mold) having the shape of FIGS. 7a or 7b is very advantageous to prevent the appearance of smiling effect or to reduce extent of the smiling effect.

The support may consist of two sheet-type support member as shown in FIGS. 3 or 4. In this embodiment, at least one support member should have the shape described above.

The support can be made of glass or any of plastic material such as acryl resin and polyolefin resin.

The present invention will now be described in more detail with reference to example and comparison example.

COMPARISON EXAMPLE 1

Surfaces of a couple of colorless, transparent sheets of polyethylene terephthalate (length: 37 cm, width: 20 cm, thickness: 180 μm) were treated with glow discharge treatment (200 V, 1.0 A) to prepare a pair of supports.

A tape of polyethylene terephthalate provided with adhesive layers on the both surfaces (width: 10 mm, thickness including the addhesive layers: 0.5 mm) was arranged on the both side portions of the hydrophilic surface of the above support. Thus arranged tape served as a spacer.

Independently, a gel-forming solution was prepared by adding a polymerization initiator consisting of 1.3 ml. of ammonium peroxodisulfate (5 wt.% aqueous solution) and 33 μl. of TEMED (N,N,N',N'-tetramethylethylenediamine) into 100 ml. of an aqueous solution consisting of 9.5 g. of acrylamide, 0.5 g. of BIS (i.e., N,N'-methylenebisacrylamide), 0.3 g. of agarose (gelation temperature: 36° C., low electroendosmosis type), 2.5 g. of polyacrylamide, 3.58 g. of disodium hydrogen phosphate 12 hydrates, 0.33 g. of sodium dihydrogen phosphate 2 hydrates, and 0.10 g. of SDS (sodium dodecyl sulfate). The gel-forming solution was introduced into the space formed by the spacer and the support and then gelation was performed to obtain a polyacrylamide gel membrane having thickness of 0.5 mm. Then, 17 slots for introducing sample were formed at equal spaces on one end portion of the gel membrane. The gel membrane was covered with the other support via the spacer so as to prepare a medium for electrophoresis.

Electrophoresis of bromophenol blue [CAS Registry No. 115-39-9] was performed according to the vertical method for 3 hours at 1000 V. of applied voltage (DC) by means of an apparatus for electrophoresis manufactured by Marisol Corp., using the above medium and a buffer solution consisting of 1.05 g. of tris(hydroxymethyl)aminomethane, 0.55 g. of boric acid, 93 mg. of EDTA.2Na and water to make it 100 ml.

Smiling effect appeared on the electrophoresis pattern as shown in FIG. 1. The migration distance at the center portion was different from that at the side portions by 3 cm.

EXAMPLE 1

Surfaces of a couple of colorless, transparent sheets of polyethylene terephthalate were treated to be made hydrophilic in the same manner as in Comparison Example 1 to obtain a pair of supports (length: 37 cm, width: 20 cm, thickness: 180 μm).

A tape of polyethylene terephthalate provided with addhesive layers on the both surfaces (width: 10 mm, thickness including the addhesive layers: 0.5 mm) was placed on both side portions of the hydrophilic surface of the above sheet. Subsequently, both side edges along one end of the support (end portion opposite to the end portion where electrophoresis should start) was so cut as to be arc-shaped having 8 cm-length straight-lined portion in the vicinity the center portion. Thus, a support having different length at the center portion and at both side portions (the difference of length between at the center portion and at both side portions was set to 4 cm.) was prepared.

A polyacrylamide gel membrane was formed on the support in the same manner as in Comparison Example 1. Then, 17 slots for sample introduction were formed at equal spaces on the non-cut end portion of the gel membrane. The gel membrane was covered with the other support to prepare a medium for electrophoresis.

Electrophoresis of bromophenol blue was performed for 3 hours under the same conditions as Comparison Example 1 except that the above medium was employed.

The pattern of electrophoresis was substantially linear as shown in FIG. 3 and the smiling effect was so small as to be neglected.

We claim:

1. An electrophoresis apparatus including a medium for electrophoresis tightly sandwiched by supports, the improvement which comprises the length of both side portions of the medium along the direction of electrophoresis is shorter than that of the center portion of the medium.

2. The apparatus of claim 1 wherein at least one end of the medium is arc-shaped whose center portion is shaped in a straight line.

3. The apparatus of claim 1 wherein one end portion opposite to the other end portion where electrophoresis starts is arc-shaped whose center portion is shaped in a straight line.

4. The apparatus of claim 1, 5 or 6 wherein the medium is a gel membrane.

5. An electrophoresis apparatus including a set of supports for tightly sandwiching a medium to be employed in a process for electrophoresis wherein the potential in the direction of electrophoresis is larger at both side portions of the medium than at the center portion thereof, wherein the length of both side portions of at least one support along the direction of electrophoresis is shorter than that of the center portion of the same support.

6. The apparatus of claim 5 wherein at least one end of the support is arc-shaped whose center portion is shaped in a straight line.

7. The apparatus of claim 5 wherein the set of supports consists of two sheet supports.

8. The apparatus of claim 1, 6 or to 7 wherein the set of supports is made of plastic material or glass.

* * * * *